United States Patent [19]

Tamabayashi et al.

[11] Patent Number: 5,302,761

[45] Date of Patent: Apr. 12, 1994

[54] TETRABROMOBISPHENOL A HAVING A LARGE PARTICLE SIZE AND PROCESS FOR ITS PRODUCTION

[75] Inventors: Hanzo Tamabayashi, Tokuyama; Shinji Kakimoto, Shinnanyo; Tetsuto Mizui, Tokuyama; Akihiko Nomura, Shinnanyo; Koji Kunimoto, Tokuyama, all of

[73] Assignee: Tosoh Corporation, Shinnanyo, Japan

[21] Appl. No.: 63,603

[22] Filed: May 19, 1993

[30] Foreign Application Priority Data

| May 19, 1992 [JP] | Japan | 4-150025 |
| May 19, 1992 [JP] | Japan | 4-150026 |
| May 19, 1992 [JP] | Japan | 4-150027 |

[51] Int. Cl.$^5$ ........................................ C07C 39/367
[52] U.S. Cl. ........................... 568/726; 568/722
[58] Field of Search .............. 568/722, 723, 726, 724, 568/774, 779, 776

[56] References Cited

U.S. PATENT DOCUMENTS

| 4,701,568 | 10/1987 | McKinnie et al. | 568/726 |
| 4,990,321 | 2/1991 | Sato et al. | 423/486 |
| 5,008,469 | 4/1991 | Eguchi et al. | 568/726 |
| 5,017,728 | 5/1991 | McKinnie et al. | 568/726 |
| 5,059,726 | 10/1991 | Eguchi et al. | 568/726 |
| 5,138,103 | 8/1992 | Eguchi et al. | 568/726 |
| 5,208,389 | 5/1993 | McKinnie et al. | 568/726 |

FOREIGN PATENT DOCUMENTS

| 2758566 | 7/1978 | Fed. Rep. of Germany | 568/726 |
| 1031500 | 6/1966 | United Kingdom . | |

OTHER PUBLICATIONS

Database WPI, Derwent Publication Ltd., AM 75-16707W, JP-A-49 110 653, Oct. 22, 1974.
Chemical Abstracts, vol. 104, No. 22, Jun. 2, 1986, AM 197560c, p. 744.

*Primary Examiner*—Werren B. Lone
*Attorney, Agent, or Firm*—Oblon, Spivak, McClelland, Maier & Neustadt

[57] ABSTRACT

Single crystals of tetrabromobisphenol A having an average particle size of from 150 to 500 μm, each having a polyhedral shape.

9 Claims, No Drawings

TETRABROMOBISPHENOL A HAVING A LARGE PARTICLE SIZE AND PROCESS FOR ITS PRODUCTION

The present invention relates to tetrabromobisphenol A (hereinafter referred to simply as TBA) of high quality having impurities reduced and having excellent powder properties as single crystals having large particle sizes, and a process for its production.

TBA is a compound useful as a flame retardant for e.g. epoxy resins and ABS resins.

TBA is used in a large amount as a flame retardant for various resins. As a reactive-type flame retardant, it is used for e.g. epoxy resins, and as an addition-type flame retardant, it is used for e.g. ABS resins. In its use as an addition-type flame retardant, a pelletized or powdery resin and a TBA powder are mixed, kneaded and then molded. However, conventional TBA is a powder difficult to handle with various problems with respect to the powder properties such as the adherence, cohesiveness and flowability. Especially, in recent years, deterioration of the working environment due to a powder dust is taken up as a problem. Further, it is poor in the thermal stability, and there is a problem of coloring during the kneading into a resin or during the molding. Furthermore, it has a problem that the productivity is poor.

TBA is produced usually by brominating bisphenol A (hereinafter referred to simply as BPA) with bromine by means of an organic solvent such as an alcohol or a halogenated hydrocarbon, adding to the reaction solution a solvent in which the solubility of TBA is small, such as water, to precipitate TBA crystals, followed by filtration and drying.

TBA produced by such a conventional method is agglomerated particles having an average particle size of from 50 to 150 μm containing a large amount of fine particles. It has a wide particle size distribution with a large content of fine particles, and therefore, it is a powder difficult to handle with strong adherence and cohesiveness and poor flowability. Further, it contains a large amount of impurities such as hydrolyzable bromine.

However, little has been proposed for the improvement of the powder properties. Methods for production of TBA have been proposed, for example, in Japanese Examined Patent Publications No. 3376/1966 and No. 15293/1966 and Japanese Unexamined Patent Publication No. 13418/1972, and purification methods have been proposed, for example, in Japanese Examined Patent Publications No. 5508/1977 and No. 25009/1986 and Japanese Unexamined Patent Publication No. 3139/1989. However, all of these proposals are concerned with the color and impurities and disclose nothing about the crystal shapes or the powder properties of TBA.

In its application to an epoxy resin in which TBA is used in a large amount as a reactive-type flame retardant, hydrolyzable bromine contained in TBA is problematic, since it adversely affects the curing reaction of the resin or the resin properties after the curing. Therefore, TBA to be used for such a purpose is required to be purified to reduce the hydrolyzable bromine content. Japanese Unexamined Patent Publication No. 3139/1989 proposes as a particularly effective purification method, a method which comprises dissolving TBA in an aromatic hydrocarbon under heating, treating the solution by dropwise adding an aqueous alkali metal solution, followed by neutralization, washing with water and cooling to precipitate crystals. Further, Japanese Unexamined Patent Publication No. 110653/1974 proposes a purification method which comprises contacting TBA with an aqueous alkali solution in a suspended state.

However, TBA obtainable by these purification methods still contained hydrolyzable bromine at a level of from 50 to 100 ppm and thus was not fully satisfactory. Besides, these methods propose nothing for the thermal stability or the improvement of the powder properties.

It is an object of the present invention to provide TBA of high quality with good thermal stability and a large particle size having the hydrolyzable bromine content reduced and having the crystal shape and the powder properties improved, which has not been satisfied by any conventional powder or conventional process therefor, and a process for its production.

For the purpose of the present invention, the hydrolyzable bromide is represented by the amount of bromide ions dissociated when TBA is dissolved in a potassium hydroxide-methanol solution and refluxed for 15 minutes, as represented by the weight ratio to TBA.

The quantitative analysis of the amount of such bromine ions can be conducted by e.g. a potentiometric titration method by means of an aqueous silver nitrate solution, or by ion liquid chromatography.

Under these circumstances, the present inventors have conducted extensive studies to reduce the impurities and to improve the powder properties. As a result, it has been found that the powder properties can be improved by converting agglomerated particles containing a substantial amount of fine particles to polyhedral single crystals having large particle sizes.

TBA is basically octahedral crystals, and it is a powder having a true specific gravity of 2. However, conventional TBA is agglomerates containing a large amount of fine particles or a powder having a wide particle size distribution, whereby the adherence and cohesiveness are strong, and the flowability is poor.

With respect to a process for its production, it has been found possible to obtain single crystals having a large particle size and to obtain TBA having the powder properties improved, by brominating BPA in an alcohol solvent, followed by addition of water for crystallization and then by filtration to obtain TBA crystals, dissolving the crystals in an alcohol solvent, followed by heating and stirring to evaporate and distill off the alcohol solvent and to precipitate crystals. Further, it has been found possible to obtain TBA of high quality having the content of hydrolyzable bromine reduced, by dissolving TBA crystals obtained by crystallization by an addition of water, followed by filtration, in an alcohol solvent, adding an aqueous alkali solution thereto, followed by distilling off the solvent. The present invention has been accomplished on the basis of this discovery.

In a method for precipitating TBA crystals, it is difficult to let crystals grow by the conventional method in which TBA is crystallized by adding a solvent in which the solubility of TBA is small, such as water, whereby the product will be agglomerated crystals containing a large amount of fine particles. Therefore, it has been unavoidable that impurities in the mother liquor are included in the crystals. Whereas, according to the method of the present invention, it has been made possible to let TBA crystals grow and to obtain single crystals having large particle sizes by the crystallization by evaporation, wherein an alcohol solvent having TBA dissolved therein, is evaporated and distilled off to concentrate and crystallize TBA. Further, by such single crystals, it has been made possible to minimize the inclusion of thermally unstable impurities in the mother liquor into the crystals and to obtain TBA of high quality.

The hydrolyzable bromine is believed to be derived from an alkyl bromide having a relatively weak carbon-bromine bond formed by the bromination of impurities in BPA and/or by bromination of side chain alkyl groups of TBA. Accordingly, it is believed possible to obtain TBA having the hydrolyzable bromine reduced, by adding alkali to hydrolyze alkyl bromides and thereby to remove bromine, followed by evaporation and crystallization to let TBA grow into single crystals having large particle sizes with little inclusion of the impurities in the mother liquor into the crystals.

The present invention thus provides a polyhedral single crystal TBA of high quality with good thermal stability and a large particle size having improved powder properties such as adherence, cohesiveness and flowability, and a process for its production.

Namely, the present invention provides single crystals of tetrabromobisphenol A having an average particle size of from 150 to 500 μm, each having a polyhedral shape.

Further, the present invention provides a process for producing tetrabromobisphenol A having a large particle size, which comprises brominating bisphenol A in an alcohol solvent, followed by addition of water for crystallization and then by filtration to obtain crystals of tetrabromobisphenol A, dissolving the crystals in an alcohol solvent, and then evaporating and distilling off the alcohol solvent to precipitate crystals.

Now, the present invention will be described in detail with reference to the preferred embodiments.

Conventional. TBA is agglomerates containing a large amount of fine particles of 45 μm or less and is a powder having a wide particle size distribution with an average particle size of from 50 to 150 μm. Further, such fine particles have irregular shapes. Therefore, the agglomerating force among particles is strong to form a powder having strong adherence and cohesiveness. This is apparent also from the fact that conventional TBA has an angle of repose of from 45° to 55° and a compressibility of from 35 to 50% as its powder properties, and thus it is a powder difficult to handle with poor flowability.

Whereas, TBA of the present invention is single crystals of a constant shape which is basically of octahedron. However, depending upon the conditions for its preparation, it may sometimes be single crystals of a truncated octahedron or of a partially modified polyhedron. It has a sharp particle size distribution with an average particle size of from 150 to 500 μm and with a small content of fine particles. Therefore, the agglomerating force among particles is weak, and the adherence and cohesiveness are extremely weak, whereby it is a powder having a good flowability with an angle of repose of from 35° to 45° and a compressibility of from 15 to 30%.

In the present invention, BPA is firstly brominated with bromine in an alcohol solvent, and after the reaction, water is added to the reaction solution to precipitate crystals of TBA, followed by filtration to obtain wet crystals. This reaction step is conducted in accordance with a known method such as a method disclosed in Japanese Examined Patent Publication No. 3376/1966. The obtained crystals are dissolved again in an alcohol solvent, and the alcohol solvent is evaporated and distilled off until crystals precipitate, under heating and stirring. Then, filtration and drying are conducted to obtain single crystal TBA of a large size.

The alcohol solvent useful for the process of the present invention may be an alkyl alcohol having at most 4 carbon atoms, and particularly preferred is methanol, ethanol or propanol. The alcohol solvent to be used for the bromination reaction and the alcohol solvent to be used for dissolving the crystals may not necessarily be the same.

The concentration of TBA at the time of dissolving the crystals in the alcohol solvent again, is not particularly limited, but is usually from 5 to 50 wt%.

The temperature for heating after dissolving the crystals in the alcohol solvent again, is at least a temperature necessary to evaporate and distill off the used alcohol solvent under atmospheric or reduced pressure. Further, the size of the crystals can be adjusted by controlling the rate of evaporating and distilling off the alcohol solvent and the amount of the distilled solvent. There is no particular limitation as to the amount of the solvent evaporated and distilled off, but it is preferred that the amount of crystals in the slurry would be at most 70 wt%, in consideration of the operation efficiency in the subsequent filtration step and the quality of TBA to be recovered.

After the evaporation for crystallization, filtration can be conducted at the same temperature as during the evaporation for crystallization. Otherwise, the slurry may further be cooled to let the crystals further grow, before the filtration. More preferably, after the filtration, the crystals are washed with e.g. water to remove the alcohol solvent.

To obtain an industrial product, it is necessary to dry the product. The drying conditions are preferably at most 180° C., preferably from 100 to 150° C., under atmospheric pressure or reduced pressure. A series of these operations can be conducted by a continuous method on an industrial scale.

Further, the amount of hydrolyzable bromine can be reduced by incorporating an operation of adding an aqueous alkali solution after dissolving the crystals of TBA again in an alcohol solvent. The aqueous alkali solution to be added is an aqueous solution of an alkali metal hydroxide or an alkali metal carbonate, such as a hydroxide or carbonate of sodium, potassium, lithium or magnesium. The concentration of the aqueous alkali solution is not particularly limited. The amount of the alkali added is usually at most 5 wt%, preferably from 0.01 to 1.0 wt%, to TBA.

As is apparent form the foregoing description, according to the process of the present invention, TBA can be produced in the form of polyhedral single crystals having large particle sizes with an average particle size of from 150 to 500 μm. With such crystals of large particle sizes, the powder properties such as adherence, cohesiveness and flowability can be improved, and the handling efficiency at the time of using it as a flame retardant for various resins is substantially improved.

Further, it is possible to produce a high quality TBA with good heat resistance, which has a small content of thermally unstable impurities in the crystals and a hydrolyzable bromine content of from 5 to 30 ppm.

Various improvements are possible by using such a high quality TBA of the present invention as a flame retardant for various resins. An ABS resin composition obtained by using it as an additive-type flame retardant, is substantially free from coloring due to the heat during the molding, whereby the processing temperature can be increased and the productivity can be improved. On the other hand, in the case of an epoxy resin composition obtained by using it as a reactive flame retardant, the curing reaction of the resin which is usually influenced by hydrolyzable bromine, and the resin properties such as thermal stability, can be remarkably improved.

Now, the present invention will be described in further detail with reference to Examples. However, it should be understood that the present invention is by no means restricted to such specific Examples.

REFERENCE EXAMPLE 1

Into a flask having a capacity of 300 ml and equipped with a thermometer, a stirrer and a condenser, 136 ml of methanol was charged, and 18.3 g of BPA was added and dissolved therein. Then, 54.3 g of bromine was dropwise added over a period of 3 hours at a temperature of from 20° to 30° C., and aging was conducted for 2 hours at the same temperature. After the aging, remaining bromine was reduced by adding an aqueous hydrazine solution. Then, 80 ml of water was added thereto over a period of 3 hours to crystallize TBA. The crystals were then collected by filtration and washed with water to obtain 42.5 g of wet crystals.

EXAMPLE 1

42.5 g of the wet crystals obtained in Reference Example 1 were charged again into the flask, and 150 ml of methanol was added thereto and the crystals were dissolved. Then, under stirring, the reaction solution was heated to a temperature of at least 65° C. to distill off methanol and to precipitate TBA crystals. When 120 ml of methanol was distilled off over a period of one hour, the heating and stirring were stopped. Precipitated crystals were collected by filtration, washed with water and dried at 120° C. to obtain 39.5 g of single crystals of TBA having large sizes.

The crystals were sieved to measure the particle size distribution, whereby particles of smaller than 45 $\mu$m were 0.5 wt%, particles of from 45 to 125 $\mu$m were 2.5 wt%, particles of from 125 to 300 $\mu$m were 80.5 wt% and particles of larger than 300 $\mu$m were 16.5 wt%. Further, the crystals were measured by a powder tester, whereby the angle of repose was 38° and the compressibility was 20%. The powder properties are shown in Table 1.

COMPARATIVE EXAMPLES 1 to 3

In the same manner as in Example 1, the powder properties of commercially available TBA were measured. The results are shown in Table 1.

TABLE 1

|  |  | Average particle size | Particles of smaller than 45 $\mu$m | Angle of repose | Compressibility |
| --- | --- | --- | --- | --- | --- |
| Example 1 |  | 250 $\mu$m | 0.5% | 38° | 20% |
| Comparative Example 1 | Commercial product A | 75 $\mu$m | 11% | 50° | 49% |
| Comparative Example 2 | Commercial product B | 160 $\mu$m | 5% | 46° | 34% |
| Comparative Example 3 | Commercial product C | 80 $\mu$m | 5% | 49° | 46% |

EXAMPLE 2

42.5 g of wet crystals prepared in the same manner as in Reference Example 1 were charged into a flask, and 150 ml of methanol was added thereto. The mixture was stirred to dissolve the crystals, and then 0.5 g of a 2% sodium hydroxide aqueous solution was added thereto. Then, under stirring, this reaction solution was heated to a temperature of at least 65° C. to distill off methanol and to precipitate TBA crystals. When 100 ml of methanol was distilled off over a period of one hour, the heating and stirring were stopped. Precipitated crystals were collected by filtration, washed with water and then dried at 120° C. to obtain 38.0 g of single crystals of TBA having large particle sizes.

The crystals were sieved to measure the particle size distribution, whereby particles of smaller than 45 $\mu$m were 0.5 wt%, particles of from 45 to 125 $\mu$m were 2 wt%, particles of from 125 to 300 $\mu$m were 80 wt% and particles of larger than 300 $\mu$m were 17.5 wt%.

The crystals were subjected to potentiometric titration by an aqueous silver nitrate solution, whereby the content of hydrolyzable bromine was found to be 10 ppm.

EXAMPLE 3

43.0 g of wet crystals were prepared in the same manner as in Reference Example 1 except that ethanol was used instead of methanol. Then, the wet crystals were charged into a flask, and 150 ml of ethanol was added thereto. The mixture was stirred to dissolve the crystals, and then 1.0 g of a 2% potassium hydroxide aqueous solution was added thereto. Then, under stirring, this reaction solution was heated to a temperature of at least 80° C. to distill off ethanol and to precipitate TBA crystals. When 100 ml of ethanol was distilled off over a period of one hour, the heating and stirring were stopped. Precipitated crystals were collected by filtration and dried at 120° C. to obtain 39.5 g of single crystals of TBA having large particle sizes.

The crystals were sieved to measure the particle size distribution, whereby particles of smaller than 45 $\mu$m were 0.5 wt%, particles of from 45 to 125 $\mu$m were 6 wt%, particles of from 125 to 300 $\mu$m were 78 wt% and particles of larger than 300 $\mu$m were 15.5 wt%.

Further, the content of hydrolyzable bromine was 15 ppm.

COMPARATIVE EXAMPLE 4

Wet crystals prepared in the same manner as in Reference Example 1 were dried at 120° C. to obtain crystals of TBA. The obtained crystals were agglomerated crystals, and the particle size distribution was measured by using sieves, whereby fine particles of smaller than 45 $\mu$m were 15 wt%, particles of from 45 to 125 $\mu$m were 65 wt%, and particles of from 125 to 300 $\mu$m were 20 wt%. Further, the content of hydrolyzable bromine was 80 ppm.

COMPARATIVE EXAMPLE 5

Wet crystals were prepared in the same manner as in Reference Example 1, except that ethanol was used instead of methanol. The wet crystals were then dried at 120° C. to obtain crystals of TBA. The obtained crystals were agglomerated crystals, and the particle size distribution was measured by using sieves, whereby fine particles of smaller than 45 μm were 20 wt%, particles of from 45 to 125 μm were 60 wt%, particles of from 125 to 300 μm were 15 wt% and particles of larger than 300 μm were 5 wt%. Further, the content of hydrolyzable bromine was 120 ppm.

We claim:

1. Single crystals of tetrabromobisphenol A having an average particle size of from 150 to 500 μm, each having a polyhedral shape.

2. The single crystals of tetrabromobisphenol A according to claim 1, which have an angle of repose of from 35° to 45° and a compressibility of from 15 to 30%.

3. The single crystals of tetrabromobisphenol A according to claim 1, which have a hydrolyzable bromine content of from 5 to 30 ppm.

4. A process for producing tetrabromobisphenol A having a large particle size, which comprises brominating bisphenol A with bromine at a temperature effective for brominating bisphenol A in an alcohol solvent, followed by addition of water for crystallization and then by filtration to obtain crystals of tetrabromobisphenol A, dissolving the crystals in an alcohol solvent, and then evaporating and distilling off the alcohol solvent to precipitate crystals and thereafter drying the crystals at 100°–180° C.

5. The process according to claim 4, wherein the alcohol solvent used for bromination or for dissolving the crystals, is methanol, ethanol or propanol.

6. The process according to claim 4, wherein the crystals are dissolved in the alcohol solvent so that the concentration of tetrabromobisphenol A is from 5 to 50 wt%.

7. A process for producing tetrabromobisphenol A of high quality, which comprises brominating bisphenol A in an alcohol solvent, followed by addition of water for crystallization and then by filtration to obtain crystals of tetrabromobisphenol A, dissolving the crystals in an alcohol solvent, adding an aqueous alkali solution thereto, and then evaporating and distilling off the alcohol solvent to precipitate crystals.

8. The process according to claim 7, wherein the aqueous alkali solution is an aqueous solution of a hydroxide or carbonate of sodium, potassium, lithium or magnesium.

9. The process according to claim 7, wherein the aqueous alkali solution is added so that the amount of alkali will be at most 5 wt% to tetrabromobisphenol A.

* * * * *